United States Patent [19]

Gardner

[11] Patent Number: 4,637,905
[45] Date of Patent: Jan. 20, 1987

[54] PROCESS OF PREPARING MICROCAPSULES OF LACTIDES OR LACTIDE COPOLYMERS WITH GLYCOLIDES AND/OR ε-CAPROLACTONES

[75] Inventor: David L. Gardner, Bellville, Ohio

[73] Assignee: Battelle Development Corporation, Columbus, Ohio

[21] Appl. No.: 722,102

[22] Filed: Apr. 11, 1985

Related U.S. Application Data

[63] Continuation-in-part of Ser. No. 466,500, Feb. 18, 1983, Pat. No. 4,532,123, which is a continuation-in-part of Ser. No. 402,164, Jul. 26, 1982, abandoned, which is a continuation-in-part of Ser. No. 354,869, Mar. 4, 1982, abandoned.

[51] Int. Cl.$^4$ .......................... A61K 9/52; B01J 13/02
[52] U.S. Cl. .................................... 264/4.3; 264/4.1; 424/19; 424/21; 424/35; 424/DIG. 7; 428/402.2; 428/402.21; 514/963
[58] Field of Search ............. 264/4.1, 4.3; 428/402.2, 402.21; 424/19, 20, 21, 35, 94, DIG. 7; 210/643; 71/DIG. 1; 514/963

[56] References Cited

U.S. PATENT DOCUMENTS

| | | | |
|---|---|---|---|
| 3,173,878 | 3/1961 | Reyes | 252/182 X |
| 3,242,051 | 3/1966 | Hiestand et al. | 264/4.3 X |
| 3,429,827 | 2/1969 | Ruus | 252/188.31 X |
| 3,493,652 | 2/1970 | Hartman | 424/35 X |
| 3,532,662 | 10/1970 | Ansdell | 523/206 X |
| 3,578,605 | 5/1971 | Baxter | 424/34 X |
| 3,725,113 | 4/1973 | Chang | 424/35 X |
| 3,773,919 | 11/1973 | Boswell et al. | 424/19 |
| 3,897,308 | 7/1975 | Li et al. | 435/177 |
| 3,922,338 | 11/1975 | Estevenel et al. | 424/21 |
| 3,962,414 | 6/1976 | Michaels | 424/19 |
| 4,016,099 | 4/1977 | Wellman et al. | 264/4.1 X |
| 4,076,774 | 2/1978 | Short | 264/4 |
| 4,111,201 | 9/1978 | Theeuwes | 424/19 X |
| 4,118,336 | 10/1978 | Morishita et al. | 424/35 X |
| 4,183,918 | 1/1980 | Asher et al. | 424/94 |
| 4,211,668 | 7/1980 | Tate | 264/4 X |
| 4,254,201 | 3/1981 | Sawai et al. | 430/111 |
| 4,530,840 | 7/1985 | Tice et al. | 514/179 |
| 4,542,025 | 9/1985 | Tice et al. | 424/78 |

FOREIGN PATENT DOCUMENTS

1169090  6/1984  Canada.

OTHER PUBLICATIONS

Chang: "Semipermeable Aqueous Microcapsules as Artificial Cells", McGill University Phd. Thesis, Montreal, (Apr. 1965), pp. 93–96.
Chang: "Artificial Cells", C. C. Thomas-Publisher, (1972), pp. 15–19 and 36–42.

Primary Examiner—Richard D. Lovering
Attorney, Agent, or Firm—Benjamin Mieliulis

[57] ABSTRACT

A process for preparing polylactide (PLA) microcapsules is described and involves dissolving PLA in a mixture of two miscible organic liquids, the higher vapor pressure liquid having solvent power for PLA and the second having little or no solvent power for PLA. The solution is prepared such that it is near its saturation point for PLA. Encapsulation of dispersed core material is achieved by vaporizing the liquid having solvent power for PLA causing phase separation of the PLA, then transferring the separated dispersion to an organic liquid having no solvent power for the PLA in order to harden the encapsulating coating. The disclosed process enables forming true microcapsules or reservoir-type devices encapsulating liquid core material particularly aqueous liquid core material and oil in water emulsion or suspensions.

6 Claims, No Drawings

PROCESS OF PREPARING MICROCAPSULES OF LACTIDES OR LACTIDE COPOLYMERS WITH GLYCOLIDES AND/OR ε-CAPROLACTONES

CROSS REFERENCE TO RELATED APPLICATIONS

This application is a continuation-in-part of applicant's co-pending application Ser. No. 466,500 Filed 2-18-83 now U.S. Pat. No. 4,532,123 which is a continuation-in-part of the applicant's application Ser. No. 402,164, now abandoned, filed on July 26, 1982, which in turn is a continuation-in-part of the applicant's prior co-pending application Ser. No. 354,869, filed Mar. 4, 1982, now abandoned.

BACKGROUND OF THE INVENTION

1. Field of the Invention

An increasingly important process for delivering a functional material to a particular locus involves the use of microcapsules. As the term is used in the art, a microcapsule contains a functional material encapsulated in a membrane.

An important application of microcapsules is in the medical arts. In this field of application, a functional drug is encapsulated in a membrane that is semipermeable to the drug. When the drug is administered to the host, the drug is transported across the semipermeable membrane to release the drug to the host.

Especially with certain polymers, such as biodegradeable polymers, a need exists for improved methods of forming microcapsules, especially true microcapsules encapsulating a liquid functional core, particularly where the liquid functional core is an aqueous liquid or a suspension in aqueous liquid. With lactides, glycolides and their copolymers, avoiding agglomeration due to their tackiness has been a major obstacle until this invention.

2. Description of the Prior Art

Encapsulation processes including microencapsulation have been known for many years. Methods of microencapsulation include: phase separation techniques, based on, for example, chilling or solvent evaporation; interfacial polycondensation, spray drying, and spraying in a fluidized bed.

Phase Separation Encapsulation is typically a process for preparing Microcapsules in which the core material to be encapsulated is dispersed, customarily by stirring, in a solvent solution of a polymer. While continuing stirring to keep the core material uniformly dispersed throughout the polymer solution, a nonsolvent liquid is added to the polymer solution to change the polymer solubility in the medium and cause a phase separation of the dissolved polymer. Depending upon the specific polymer/solvent system, the polymer either precipitates from the solution or two immiscible liquid phases are produced, one of which is rich in polymer and polymer solvent and poor in nonsolvent, and the second of which is rich in nonsolvent and poor in solvent and polymer. Under certain conditions, the polymer rich phase will migrate to the interface between the dispersed droplets/particles and the continuous phase (non-solvent rich dispersing medium). The suspended particles of the core material are encapsulated with the polymer and are subsequently hardened and recovered from the solvent/nonsolvent medium.

Phase separation relying on solvent evaporation typically involves dissolving the wall material in a water immiscible organic solvent. The core material is also added to the organic solvent forming a suspension or solution of wall material, core material and solvent.

This suspension or solution is then added to a beaker of water with vigorous stirring forming an emulsion. Evaporation of the organic solvent under vacuum causes the precipitation and formation of solid microcapsules.

In almost all of the prior art processes involving lactides, glycolides and their copolymers, the capsules formed are not true microcapsules in the sense of being reservoir type devices. In other words typically the microcapsules which are formed comprise a wall material encapsulating a solid core, the solid core typically consisting of solid drug particles homogeneously dispersed in a solid polymer matrix. Thus the prior art product is closer to a microsphere than a true capsule.

A need exists in the art for reliable methods for forming true microcapsules from lactides, glycolides, and their copolymers, i.e., reservoir type devices, encapsulating a liquid core particularly an aqueous liquid core, oil in water emulsion or suspension.

SUMMARY OF THE INVENTION

It is an object of the present invention to disclose a method of preparing true microcapsules encapsulating a core material, especially a core material which is a liquid material.

It is an object of the present invention to disclose a method of preparing a microcapsule comprising wall material forming a reservoir type device encapsulating an aqueous liquid or a suspension in aqueous liquid.

It is an object of the present invention to disclose a process of preparing a true microcapsule encapsulating an aqueous liquid functional core and having a zero order release profile.

The invention is directed to a method of preparing novel microcapsules especially of biodegradeable polymers such as d,l-polylactide (PLA) and its copolymers which can be employed to release a wide variety of drugs to a host especially via oral or subcutaneous injection routes.

This invention and application describes a novel process for preparing microcapsules relying on evaporation only to initiate wall formation. The microcapsule formed has an aqueous solution or suspension of functional material encapsulated therein. The invention is directed to methods of preparing such microcapsules, especially of PLA wall material.

The microcapsules of the prior art, since they encapsulate a solid core homogeneously dispersed in a polymer matrix typically have a first order release profile but are incapable of a zero order release profile absent special and costly modifications such as those involving increasing the drug concentration gradient with distance into the interior of the solid core. Zero order release microcapsules of lactides, glycolides and their copolymers involving aqueous liquid cores have been unknown prior to this invention.

The present invention by enabling encapsulation of a liquid core such as an aqueous suspension provides a true microcapsule meaning a reservoir type device. Since the core is a liquid suspension of dissolved and excess solid drug molecules, then, as drug molecules diffuse through the capsule wall, additional drug goes into solution within the capsule maintaining uniform concentration within the capsule solution thus yielding a microcapsule having a zero order release profile for at least 90% of its useful life.

DEFINED TERMS

As an aid in interpreting the descriptions of the inventions which follow, the following terms will have the special meanings set forth below.

"Microcapsule" is an article of manufacture having a Functional Core Material encapsulated within a polymeric membrane. While Microcapsules may have essentially any physical form, they customarily are essentially spherical in shape and customarily have average diameters in the range of about 1 μm to 2,000 mm.

"Functional Core Material" is the aqueous liquid, oil in water emulsion or suspension, or aqueous soluble solid sought to be encapsulated in a microcapsule.

"Encapsulating Process" is any process for encapsulating a Functional Core Material in a polymeric membrane.

"Drug" is a Functional Agent having a desirable beneficial physiological effect upon a host.

"PLA" is a polymer of lactic acid. PLA polymers as such are known in the art. See U.S. Pat. No. 3,991,776. For clarity, as used in this invention the term "PLA" is defined and understood to include polymers and copolymers of lactic acid, d,1-polylactide, 1-lactide or copolymers of or with glycolide and/or ε-caprolactone.

"Dalton" is a term becoming increasingly popular in the art to designate molecular weight. A Dalton number is numerically equivalent to a gram molecular weight. By way of example, the Dalton number of sucrose is 342.

"Solvent" is an organic liquid having the power to dissolve at least 0.1 weight % of a designated polymer of interest at ambient temperature.

"Nonsolvent" is an organic liquid miscible with a solvent and having little or no solvent power for a designated polymer of interest at ambient temperature.

DETAILED DESCRIPTION

The present invention provides a reliable process for preparing PLA microcapsules and PLA copolymer microcapsules. In the first step of this process, the PLA or copolymer is dissolved in a miscible mixture of a solvent and a nonsolvent. The solvent and nonsolvent will be employed in a ratio such that the resulting PLA or copolymer solution prepared therefrom is very close to its phase separation point. This phase separation point, referred to as cloud point can be judged from the solution's turbidity. As will be readily recognized, the precise ratio of the solvent and nonsolvent employed will depend both upon the specific solvent and nonsolvent employed as well as the concentration of PLA or copolymer desired in the solution at its phase separation point. A convenient way to prepare the PLA or copolymer solution is to dissolve the PLA or copolymer is pure solvent, add sufficient nonsolvent to cause incipient PLA or copolymer phase separation i.e. reach the cloud point, and then add The smallest quantity of solvent to redissolve the small quantity of separated PLA or copolymer.

For reasons which will become apparent from the subsequent descriptions, it is important that the solvent employed have a vapor pressure significantly higher than the vapor pressure of the nonsolvent at the temperature employed to precipitate PLA in the third step of the process subsequently described. References to PLA are equally applicable to PLA copolymers.

In the second step of the process, the PLAcontaining homogeneous solution prepared in the first step of the process is vigorously agitated and the functional core material is added. The agitation provided will be sufficient to disperse these materials uniformly throughout the continuous PLA-containing solvent solution as a fine suspension.

In the third step of the process, agitation is continued to maintain the core material dispersed throughout the PLA-containing solvent solution. Conditions are established to vaporize solvent and nonsolvent from the suspension. While both solvent and nonsolvent will be vaporized and removed from the suspension, the solvent will be removed in greater quantities that the nonsolvent by reason of the solvent's higher vapor pressure. the preferential removal of solvent from the system, of course, changes the ratio of the solvent and nonsolvent liquid in which the PLA is dissolved. Since the PLA-containing solution as prepared is near its saturation point for PLA, as the composition of the solvent/nonsolvent medium is changed, the PLA will undergo a phase separation. The phase separated PLA migrates to the surface of the finely dispersed core droplets or particles and begins encapsulation thereof. After a sufficient quantity of PLA has encapsulated the core droplets or particles, the resulting complex dispersion is ready for transfer to the fourth step of the process.

In the fourth step of the process, the complex suspension from the third step of the process is transferred into an agitated mass of nonsolvent. Upon contacting the nonsolvent to which the suspension is added, any PLA remaining dissolved in the initial solvent solution is precipitated. A second phenomenon which is believed to occur is the extraction of the residual solvent from the PLA membrane.

In carrying out the process, the solvent/nonsolvent mixture employed in the first step of the process should have the requisite solubility to dissolve a convenient quantity of PLA. It is desirable to employ solvent/nonsolvent mixtures which will dissolve at least about 0.3 part by weight of PLA per 100 parts by volume of solvent/nonsolvent mixture at ambient temperature. It also is desirable to employ solvent/nonsolvent mixtures having relatively sharp changes in PLA solubility capacity with temperature. The presently preferred solvents for use in the process are halogenated hydrocarbons having an atmospheric boiling point of less than about 65° C. and esters formed between alkanols containing 1–4 carbon atoms and alkanoic acids containing 1–4 carbon atoms. Suitable halogenated hydrocarbons of this class include methylene chloride and chloroform. The preferred ester is ethyl acetate. The nonsolvents presently preferred for use in the process are hexane, cyclohexane, heptane, selected mineral spirits, nonane, Freon ® (registered trademark of E. I. Dupont), TF and the like.

In the third step of the process, after the core materials are uniformly dispersed throughout the polymer solution, conditions are established to vaporize the solvent and nonsolvent from the suspension. This can be done by reducing the pressure on the suspension by drawing a slight vacuum on the system or supplying heat to the suspension, or both, the preferred method being to merely vigorously agitate the polymer solution to effect evaporation. In the embodiment of the invention in which methylene chloride or chloroform is employed as the solvent and an aliphatic hydrocarbon, such as hexane or heptane, is employed as the nonsolvent, vigorous agitation is sufficient to supply the small quantity of energy required to vaporize the requisite quantity of solvent to initiate phase separation of the PLA.

In carrying out the fourth step of the process, care should be exercised to transfer the entire suspension from the third step of the process into the agitated nonsolvent before the encapsulated core materials begin agglomeration into oversized aggregates, presumably by reason of the somewhat tacky nature of the encapsulating PLA membrane at this stage of the process. The appropriate point at which the suspension should be transferred to the agitated nonsolvent can be readily established with a minimum of experimentation. It has been the applicant's observation that in preparing batches of the size subsequently described in the working examples, the suspension should be transferred to the agitated nonsolvent in a time period of between 3 and 10 minutes, preferably 4–7 minutes after the initial phase separation of the PLA is observed in the third step of the process. This time factor, it is anticipated, can vary depending on the specific polymer and specific molecular weight involved.

In the final step of the process, it is desirable to transfer the suspension from the third step of the process into a large excess of the nonsolvent, e.g., 3–20 times the total volume of the solvent solution employed in the first step of the process.

The process described above is carried out under essentially isothermal conditions and preferably at ambient temperatures.

Although not presently preferred, it is possible to heat the PLA solution in the first step of the process to a temperature somewhat above ambient temperature. As the temperature drops in carrying out the second and third steps of the process, the lowering of the temperature accelerates the phase separation of the PLA.

The present process differs from prior art phase separation processes in that this process involves evaporation only to effect phase separation and initiate formation of a capsule wall. This entails evaporation over only a limited range of concentration. The prior art involving lactide, glycolide and its copolymers relies on evaporation to completely form what is essentially a microbead.

Additionally the present invention uniquely can add an aqueous functional core. This can be, for example, a saturated suspension of drug in water. Optional additional ingredients such as modifiers and thickeners affecting drug solubility thus ultimately affecting drug diffusion through the capsule wall, can also be included. The present invention can also be used to encapsulate an oil in water emulsion within the microcapsule. An oil in water emulsion within a true microcapsule of wall material of lactide, glycolide or their copolymers is not believed achievable by any known prior art method thus in many respects this invention is a method significantly advancing the scope of encapsulation technology for these polymers enabling encapsulation of materials and suspensions unachievable previously.

The following examples are set forth to illustrate certain principles and practices of the invention to those skilled in the art.

The examples are intended as illustrative rather than a limit on the scope of the invention.

EXAMPLES

1. Preparation of microcapsules of d,1-polylactide, molecular weight 55,000.

1.5 grams of d,1-polylactide were dissolved in 75 ml of dichloromethane plus 75 ml of Sohio® 3440 (mineral spirits, nonsolvent for PLA). The aqueous core material was 12 grams of phosphate buffer (0.1M, pH 7.3).

The core solution was added to the polymer solution to disperse the core solution. After stirring for 25 minutes and while stirring, 4–5 ml of the solution was pulled over or quenched into 200 ml of 50% Sohio 3440 and n-heptane which contains 8 drops of surfactant or emulsifier Span 80. The solution was slowly stirred for 10 minutes - 15 minutes and then filtered.

2. Preparation of PLA microcapsules or minimicrocapsules comprised of a 60/40 ratio of lactide to glycolide.

1.5 grams of a 60/40 ratio polymer of glycolide/lacide was dissolved in 75 ml of dichloromethane plus 22 ml of Sohio® 3440. The core material was 12 grams of 1% bovine serum albumin in 0.1M phosphate buffer as in Example 1. The core was prepared by adding 0.5 g bovine albumin to 49.5 g 0.1M PB and stirring until dissolved. The core solution was added to the copolymer solution, then pulled into quench vials containing approx. 13 ml Sohio® 3440 and 1 drop of Span® 80 (Atlas, Sorbitan Monooleate, N.F.). Capsules were recovered at 15 seconds, 40 seconds, 1 minute, 2 minutes, 4 minutes, and 6 minutes. Intact capsules were obtained from the 40 second quench.

3. Preparation of microcapsules using 80/20 ratio of d,1-lactide to ε-caprolactone as wall material (Molecular Weight approx. 40,000).

The core material was 1% bovine serum albumin in 0.1M phosphate buffer prepared as in Example 2. 1.5 grams of an 80/20 ratio of d,1-lactide/ε-caprolactone was dissolved in 75 ml of dichloromethane plus 80 ml of Sohio® 3440. Using a 250 ml extraction flask, the core solution was added to the polymer solution to disperse the core solution. Following stirring the solution was pulled into quench vials containing 13 ml of Sohio® 3440 and 1 drop Span® 80 at 20 and 40 seconds and 1,2,3,6, and 8 minutes. Some microcapsules were noted. Aggregation reversed as quenching exceeded 2 minutes.

In a repeated run, stirring was slowed. During quenching the solvent was decanted twice and replaced with fresh 3440 solution. The 20 second quench had reduced aggregation, capsules did not aggregate further after setting overnight.

4. Preparation of microcapsules using 1-lactide as wall material.

1.5 grams of 1-lactide was dissolved in 60 ml dichloromethane plus 68 ml of nonane. The core material was 12 grams of 0.1M phosphate buffer. The core solution was added to the polymer solution to disperse the core solution. The solution was slowly stirred for 20 minutes. Quench vials contained 25 mls Sohio® 3440 and 1 drop Span® 80. The solution was pulled in the quench vials at 2,4,6,10, and 20 minutes. The four minute quench vials showed the best capsules.

5. Same as example 4 except the 1-lactide was dissolved in 75 ml of dichloromethane plus 70 mls of Sohio® 3440. Capsules were obtained at 2 and 5 min. quenches.

While the process and products herein described constitute preferred embodiments of the invention, it is to be understood that the invention is not limited to these precise processes and products, and that changes may be made therein without departing from the scope of the invention which is defined in the appended claims.

What is claimed is:

1. A process for preparing a microcapsule having an aqueous functional core material encapsulated in a PLA which comprises:
   (a) dissolving PLA in a mixture of two miscible organic liquids, the first being a liquid having solvent power for PLA and the second having little or no solvent power for PLA, the two liquids being present in a ratio such that the solution is near its saturation point for PLA, the liquid having solvent power for PLA having a vapor pressure significantly higher than the vapor pressure of the second liquid,
   (b) agitating the solution of step (a) and adding thereto an aqueous functional core material so as to uniformly disperse the aqueous functional core material as a fine suspension throughout the continuous liquid phase having the PLA dissolved therein, and
   (c) vaporizing the liquid having solvent power for PLA from the suspension of step (b) while continuing agitation so as to cause phase separation of the PLA and encapsulation of the finely dispersed aqueous functional core material with PLA, and
   (d) transferring the dispersion of step (c) into an agitated mass of an organic liquid having little or no solvent power for PLA to precipitate any remaining dissolved PLA and harden the PLA which has encapsulated the aqueous functional core material.

2. The process of claim 1 wherein the PLA is a polymer or copolymer comprised of monomers selected from the group consisting of lactic acid, d,1-lactide, 1-lactide, glycolide, and ε-caprolactone.

3. The process of claim 2 in which the liquid having solvent power for PLA is a halogenated hydrocarbon or an ester formed between an alkanol containing 1–4 carbon atoms and an alkanoic acid containing 1–4 carbon atoms and the liquid having little or no solvent power for PLA is a liquid hydrocarbon.

4. The process of claim 3 in which the solvent is dichloromethane, chloroform or ethyl acetate.

5. The process for claim 4 in which each step of the process is carried out at essentially ambient temperature with the energy required to vaporize the solvent liquid in step (c) being provided by the agitation of the suspension.

6. The process of claim 3 in which each step of the process is carried out at essentially ambient temperature with the energy required to vaporize the solvent liquid in step (c) being provided by the agitation of the suspension.

* * * * *